(12) United States Patent
Vollenweider

(10) Patent No.: US 8,994,942 B2
(45) Date of Patent: Mar. 31, 2015

(54) METHOD FOR IDENTIFYING INTERFERENCE OBJECT IN SCATTER VOLUME OF OPTICAL FIRE DETECTOR AND OPTICAL FIRE DETECTOR

(71) Applicant: Walter Vollenweider, Steinhausen (CH)

(72) Inventor: Walter Vollenweider, Steinhausen (CH)

(73) Assignee: Siemens Aktiengesellschaft, Munich (DE)

( * ) Notice: Subject to any disclaimer, the term of this patent is extended or adjusted under 35 U.S.C. 154(b) by 190 days.

(21) Appl. No.: 13/720,751

(22) Filed: Dec. 19, 2012

(65) Prior Publication Data

US 2013/0201479 A1 Aug. 8, 2013

(30) Foreign Application Priority Data

Dec. 20, 2011 (EP) .................................... 11194708

(51) Int. Cl.
*G01N 21/00* (2006.01)
*G01N 21/53* (2006.01)
*G08B 17/107* (2006.01)

(52) U.S. Cl.
CPC .............. *G01N 21/53* (2013.01); *G08B 17/107* (2013.01)
USPC ........... 356/343; 356/438; 250/574; 340/630; 340/577

(58) Field of Classification Search
USPC ........... 356/335–343, 432–440, 237.1–237.5; 250/573–575, 559.16; 340/630, 628, 340/577
See application file for complete search history.

(56) References Cited

U.S. PATENT DOCUMENTS

| | | | |
|---|---|---|---|
| 4,242,673 A * | 12/1980 | Cooper | 340/630 |
| 4,642,615 A * | 2/1987 | Suzuki | 340/630 |
| 5,381,130 A | 1/1995 | Thuillard et al. | |
| 6,828,913 B2 | 12/2004 | Oppelt et al. | |
| 7,551,277 B2 | 6/2009 | Cole | |
| 7,724,367 B2 | 5/2010 | Cole | |
| 7,738,098 B2 | 6/2010 | Cole | |
| 7,978,087 B2 * | 7/2011 | Siber et al. | 340/630 |
| 2002/0153499 A1 * | 10/2002 | Oppelt et al. | 250/559.16 |
| 2008/0137088 A1 * | 6/2008 | Wagner | 356/446 |

FOREIGN PATENT DOCUMENTS

| | | |
|---|---|---|
| DE | 101 18 913 A1 | 11/2002 |
| EP | 0 076 338 A1 | 4/1983 |
| EP | 0 530 723 A1 | 3/1993 |
| EP | 2 112 639 A2 | 10/2009 |
| EP | 11194708.1 | 12/2011 |

OTHER PUBLICATIONS

Chinese Office Action issued Sep. 3, 2014 in corresponding Chinese Patent Application No. 201210557676.1.

* cited by examiner

*Primary Examiner* — Hoa Pham
(74) *Attorney, Agent, or Firm* — Staas & Halsey LLP

(57) ABSTRACT

An interference object is identified in a scatter volume of an optical fire detector, which operates according to the scattered light principle. To achieve a higher level of interference protection using a simple structure in a compact fire detector, a common scatter volume is used instead of separate scatter volumes.

19 Claims, 1 Drawing Sheet

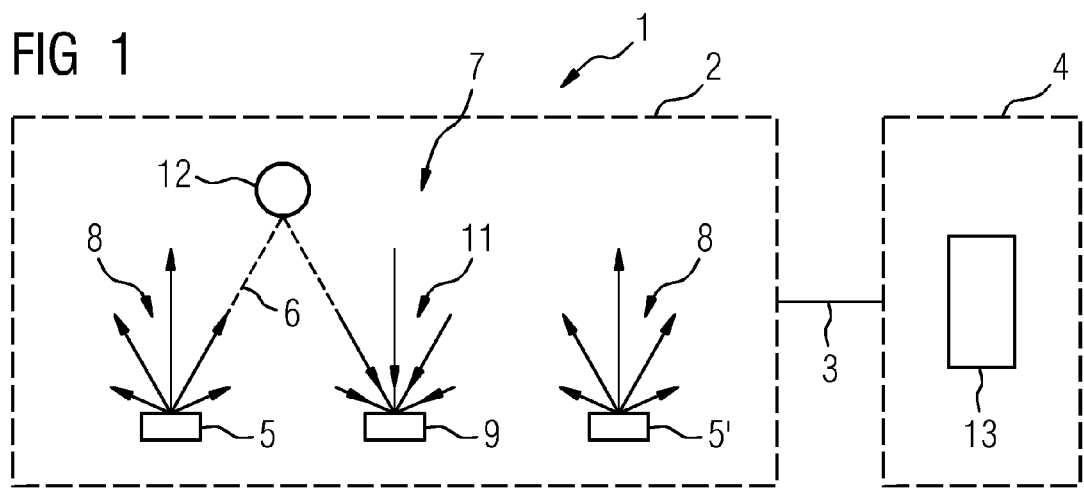
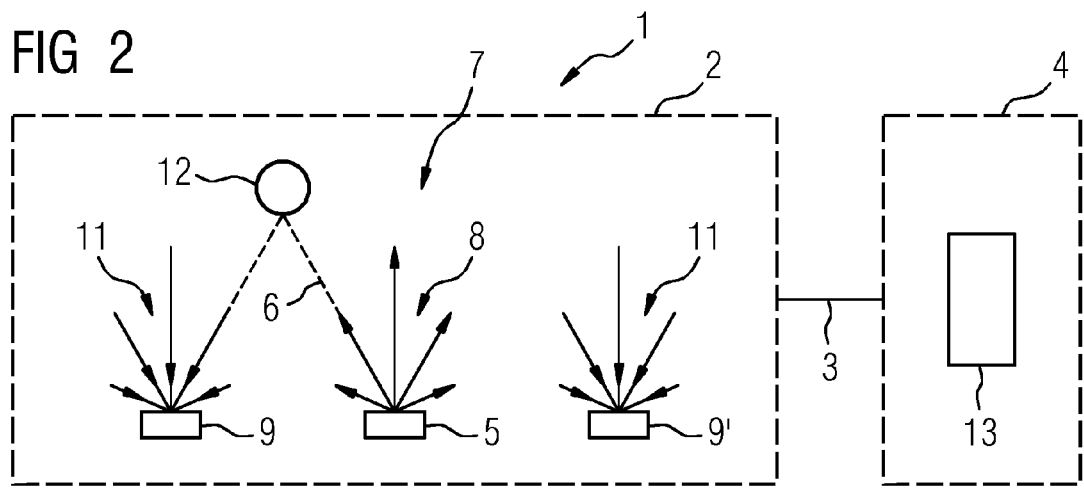
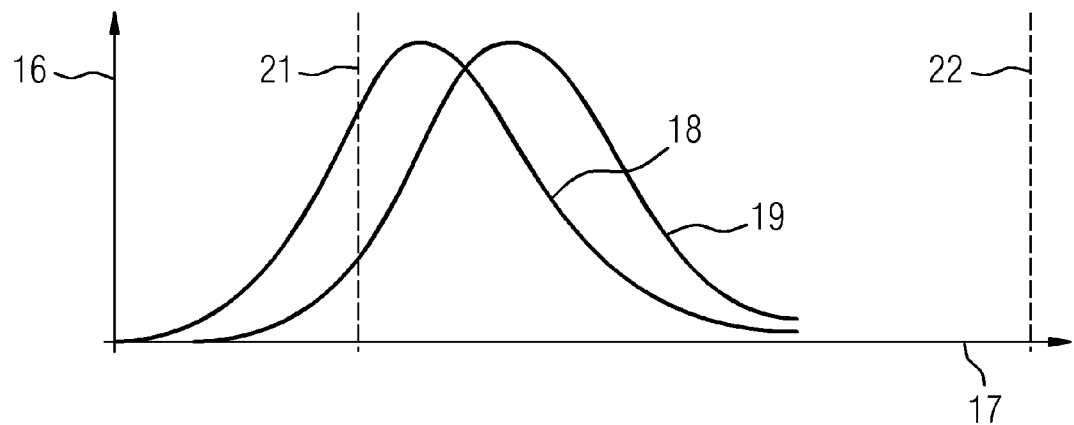

METHOD FOR IDENTIFYING INTERFERENCE OBJECT IN SCATTER VOLUME OF OPTICAL FIRE DETECTOR AND OPTICAL FIRE DETECTOR

CROSS REFERENCE TO RELATED APPLICATIONS

This application is based on and hereby claims priority to European Application No. 11194708 filed on Dec. 20, 2011, the contents of which are hereby incorporated by reference.

BACKGROUND

Described below is a method for identifying an interference object in a scatter volume of an optical fire detector, which operates according to the scattered light principle. Also described below is an optical fire detector.

In optical smoke detectors it can happen that foreign objects, for example insects, trigger false alarms. It can therefore be expedient to use a number of sensor systems, which monitor adjacent volumes. If the sensor systems detect the same or a similar value for the scattered radiation, it can be assumed that the scatter results from a fairly homogeneous medium. It can thus be assumed that it is very probably smoke. If very different values are detected however, it must be a very non-homogeneous medium. It could be smoke occurring in swathes. However it is known from practical experience that smoke from a fire that normally occurs reaches the environment of a fire detector in a fairly uniform manner, so an upper value can be assumed for non-homogeneity. If the difference between the measured values is above this limit, it must be assumed that the scatter is caused for example by dust occurring spasmodically, by swathes of vapor, by an insect or by another object. It is then permissible to generate a fault message not an alarm or at least to delay the alarm.

Corresponding arrangements have been known for some time. WO 2005/069242 thus discloses the use of locationally distanced scatter volumes and the comparison of the light scattered in the volumes. The presence of an interference object is then concluded from the result of the comparison. It is then necessary to determine separate volumes, which requires a certain outlay and in particular cannot happen without structural elements which take up a certain amount of space.

An arrangement is even known, with which it is possible to use a mechanical arrangement to deflect the emitted light beam in a specific manner, thereby searching for interfering objects in the scatter volume in the manner of a searchlight. This arrangement also involves a high level of outlay and requires a lot of space.

In instances where a particularly small sensor volume is desired, for example in an alarm that is to be particularly flat so that it can be mounted unobtrusively below the ceiling, these known ways of defining separate scatter volumes are very obtrusive.

SUMMARY

One aspect is to achieve a higher level of interference protection with a simple structure in a compact fire detector.

The advantages and embodiments described below in relation to the method also apply correspondingly to the fire detector and vice versa.

The method for identifying an interference object in a scatter volume of an optical fire detector, which operates according to the scattered light principle, uses at least two scattered light arrangements. The measured radiation is converted to scatter signals and the scatter signals are then evaluated to identify an interference object, by comparing them with one another. Provision is made here for the measured radiation to be acquired from a common scatter volume.

The optical fire detector may be an open scattered light smoke detector, in other words an open smoke detector model operating according to the scattered light principle. The common or the respective common scatter volume is outside the open smoke detector.

It is a basic concept of the method and structure described below that the desired interference protection is achieved without requiring separate scatter volumes. To this end a common scatter volume is used. According to the method, for this purpose the scatter volumes of the at least two scattered light arrangements used correspond at least partially. This means that the at least two scatter volumes overlap at least partially. A particularly simple structure can be achieved if there is only one scatter volume, in other words the scatter volumes of the scattered light arrangements used are identical.

This is advantageously achieved in that the transmitters and receivers have a transmit and receive characteristic, which corresponds essentially to the Lambert type. According to the beam characteristic of a Lambert emitter this light radiates into infinity, with an intensity which decreases as the angle between an emitted beam and the surface of the emitter becomes smaller, the intensity however being a function of the direction when the angle has a defined value. Therefore non-uniform illumination is associated with uniform emission. In other words the common scatter volume is illuminated in a non-uniform manner.

It is desirable that no further components of the open smoke detector are located between the respective transmitter and the respective receiver of the scattered light arrangements on the one hand and the opposing scatter volume on the other hand. In particular no transparent housing parts in a housing of the open smoke detector.

The open smoke detector in question may have a circuit carrier accommodated in the housing of the smoke detector. The circuit carrier has an at least essentially planar mounting surface, on which the respective transmitter and the respective receiver of the scattered light arrangements are disposed in a planar manner, so that the main transmit direction of the respective transmitter, the main receive direction of the respective receiver and the surface normal of the mounting surface or circuit carrier are parallel to one another. The respective transmitter and the respective receiver may be SMD components.

Light-emitting diodes, which are provided with a transparent cover, which are not configured in the manner of a lens but are essentially flat, are similar to Lambert emitters and are therefore may be used as transmitters in the scattered light arrangements.

If we understand the scatter volume of a scattered light arrangement to be the overlap region of the beam paths from transmitter and receiver and the radiation diagram for the transmitter and receiver corresponds essentially to the Lambert type, the beam paths of transmitter and receiver intersect everywhere. In other words the scattered light arrangements do not provide a clearly defined scatter volume.

According to the structure described below, no separating walls are used to delimit the scatter volumes of the scattered light arrangements used from one another. However there can be walls between the transmitters and receivers, which prevent light passing directly, without being scattered by smoke particles, from the transmitter to the receiver.

According to the method described below, the common scatter volume is viewed at different angles. This is ensured in that the scattered light arrangements used have different beam paths. This is advantageously achieved in that the scattered light arrangements differ from one another at least in the geometric arrangement of at least one of their optical components.

A particularly small structural outlay is required and particularly little space is necessary, if the scattered light arrangements use commonly utilized transmitters or receivers. In other words the one scattered light arrangement shares at least one transmitter or at least one receiver with the other scattered light arrangement.

In the simplest instance two separately disposed transmitters are combined with a common receiver, so that the first transmitter and the receiver form the first scattered light arrangement and the second transmitter and the receiver form the second scattered light arrangement. The different beam paths then result from the different radiation axes.

As an alternative a transmitter with two separately disposed receivers can be used, the transmitter with the first receiver forming the first scattered light arrangement and the transmitter with the second receiver forming the second scattered light arrangement. The different beam paths then result from the different receive axes.

In a further embodiment, a number of transmitters and a number of receivers are used. This is particularly advantageous, because one receive signal can be determined with every combination of one transmitter and one receiver. All the receive signals can be used by a suitable algorithm to differentiate interference objects from smoke. The algorithm can perform this task more effectively and reliably with every additional input variable. Also one transmitter and one receiver can be combined in each instance in such a manner that they give the impression of a unit. If two transmitters are present and the receiver is disposed in the center between the two transmitters, three optical units are visible. If in contrast one transmitter and one receiver respectively are combined to form a unit, only two optical units are visible.

In a development of the core concept, one or more transmitters can be used, which emit light of different wavelengths. This produces further, particularly advantageous configuration and evaluation options.

The scatter signals are evaluated by comparison, with their quotient advantageously being determined and the quotient being compared with a lower and upper limit value.

A more comprehensive evaluation can result if the pattern of the quotient over time is recorded and compared with known patterns.

A higher level of interference protection can be achieved with a simple structure and therefore particularly economically, in that interference objects can be differentiated reliably from smoke particles. The embodiment of the fire detector is simple and comparatively compact, so that only a little space is required. The method described below is therefore particularly suitable for fire detectors, as can be incorporated for example in room ceilings.

BRIEF DESCRIPTION OF THE DRAWINGS

The properties, features and advantages described above and the manner in which they are achieved will become clearer and more readily comprehensible in conjunction with the description which follows of the exemplary embodiments set out in more detail in conjunction with the drawings, in which:

FIG. 1 is a schematic diagram explaining the principle of the light scatter with two transmitters and one receiver, FIG. 2 is a schematic diagram with one transmitter and two receivers, FIG. 3 is a graph of backscatter signals as a function of particle size when using a number of transmitters with different wavelengths.

DETAILED DESCRIPTION OF THE PREFERRED EMBODIMENT

All the figures simply show the structure described below with its essential components. Identical reference characters here correspond to elements of identical or comparable function.

The optical fire detector 1 described below operates as a scattered light smoke detector and includes a detection unit 2 operating according to the scattered light principle and an electronic evaluation unit 4 connected thereto by a connecting line 3.

In a first configuration, as illustrated in FIG. 1, a first radiation source (transmitter) 5 in the detection unit 2 emits light of a defined wavelength. This light passes along a radiation axis 6 into the scatter volume 7 of the fire detector 1.

The first transmitter 5 is for example a light-emitting diode without additional optical elements, such as lenses or mirrors for example. It can be a GaAs-based or similar LED for example. The radiating part of the light-emitting diode is a crystal, which can be regarded as a uniformly illuminating surface. Light is therefore radiated in a manner described by a radiation diagram 8, as illustrated schematically in FIG. 1, which essentially corresponds to the Lambert type. The first transmitter 5 illuminates a scatter volume 7. The scatter volume 7 here extends essentially into infinity. However the scatter volume 7 is not illuminated uniformly but according to the radiation diagram 8.

A second transmitter 5' at a distance from the first transmitter 5 radiates light of a defined wavelength. The second transmitter 5' is of identical structure to the first transmitter 5 and radiates light according to a radiation diagram 8, which is at least similar to the radiation diagram of the first transmitter 5. The light from the second transmitter 5' passes along a second radiation axis 6 into the identical scatter volume 7. This second transmitter 5' also illuminates the scatter volume 7 in a non-uniform manner and in some instances into infinity. The two transmitters 5, 5' and the receiver 9 in between are typically disposed on a circuit carrier (not shown), for example on a printed circuit board with a planar mounting surface. The distance between the respective transmitter 5, 5' and the receiver 9 may be shorter than 1 cm.

In the example in FIG. 1 the main transmit direction of the two transmitters 5, 5' is symbolized by an arrow running vertically from bottom to top in the image plane. The main receive direction of the receiver 9 is symbolized by an arrow running vertically from top to bottom.

The two main transmit directions and the main receive direction can also be referred to as optical axes. In particular they form the axes of symmetry of the essentially rotationally symmetrical Lambert type transmit and receive characteristics of the transmitters 5, 5' and the receiver 9.

A photodiode for example is used as an optical radiation receiver 9 to receive the scattered light, essentially having the properties of a light-sensitive surface, so that its receive characteristic can be described by a radiation diagram 11, which in turn corresponds essentially to the Lambert type. The receiver 9 receives light from the common scatter volume 7, with light radiated back from infinity also being received in principle in some instances.

Located in the scatter volume 7 is a body 12 to be detected. This can be a smoke particle or even an interfering object, for example a dust particle, an insect or some other large object.

Light from the first transmitter 5 strikes this body 12 on the path and is backscattered onto the receiver 9. Light from the second transmitter 5' also reaches the body 12 and is backscattered onto the receiver 9. For purposes of clarity however this second path is not shown in FIG. 1.

Because the path from the first transmitter 5 to the body 12 is different from the path from the second transmitter 5' to the body 12, different quantities of light are backscattered from the two transmitters 5, 5' to the receiver 9, unless the object is by chance in a position in which the arrangement becomes symmetrical. By comparing the backscattered light originating from the first transmitter 5 and the second transmitter 5', it is possible to estimate how far the body 12 is away from a symmetrical position.

If the body 12 is a smoke particle and part of a fairly homogeneous smoke cloud, the observation described above is not possible. There are then a very large number of uniformly distributed bodies present. These bodies are backscattered in a non-uniform manner in the individual light originating from the two transmitters 5, 5'. Overall however the differences balance one another out, so that approximately the same quantity of light is backscattered from the two transmitters 5, 5' to the receiver 9.

If a different quantity of light is backscattered from the two transmitters 5, 5' to the receiver 9, the body 12 is very probably an interference object, as described below in more detail in conjunction with the evaluation of the scatter signals.

As well as the detection unit 2, in which the measured radiation is converted to scatter signals after being picked up by the receiver 9, FIG. 1 also shows the electronic evaluation unit 4, in which the scatter signals are evaluated. The evaluation here takes place in the form of a comparison of the determined scatter intensities. A comparison is then made with stored values and/or the results are evaluated based on other criteria. Then, depending on the result, at least one alarm signal is generated or a fault message is generated and an alarm is delayed.

The electronic evaluation unit 4 may be implemented by a processor-protected processing unit, for example by microcontroller 13. This may have integrated analog/digital converters to capture the two scattered light signals and digital/analog converters and/or digital output ports to output the result signals or the fire detectors. The evaluation unit 4 may be implemented by a suitable software program executed on the microcontroller 13.

The arrangement described in conjunction with FIG. 1 allows the fire detector 1 to be operated with a total of three main components, namely two radiation sources (transmitters) 5, 5' and one receiver 9. It is not necessary to use a second receiver, so the structural outlay is comparatively low.

As an alternative to this arrangement, in which the two optical transmitters 5, 5' alternately radiate light into the scatter volume 7 and the common optical receiver 9 is configured to receive radiation from both transmitters 5, 5', a further arrangement is possible, in which only three components are also used, namely a common transmitter 5 and two receivers 9, 9'. An arrangement of this type is illustrated in FIG. 2, with the arrangement of the components corresponding to the first embodiment with the transmitters 5 and receivers 9 transposed. Since optical receivers 9 are generally more expensive than transmitters 5, the component costs of this variant are higher. In contrast only one transmitter 5 has to be supplied with electric power, so the power consumption and therefore the operating costs are lower. The two receivers 9, 9' and the transmitter 5 in between are typically disposed on a circuit carrier (not shown), for example a printed circuit board, with a planar mounting surface. The distance between the respective receiver 9, 9' and the transmitter 5 may be shorter than 1 cm.

In the example in FIG. 2 the main receive direction of the two receivers 9, 9' is symbolized by an arrow running vertically from top to bottom in the image plane. The main transmit direction of the transmitter 5 is symbolized by an arrow running vertically from bottom to top.

The backscattered signals originating from two transmitters 5, 5' (FIG. 1) or received by two receivers 9, 9' (FIG. 2) may be compared by the evaluation unit 4, by determining their quotient. This means that the result is not a function of the size or number of the smoke particles or interference objects, but only of their position. Other expedient methods can however also be used, which give a similar result. If the backscattering medium is homogeneous, the quotient will assume the value 1. In contrast the quotient will be different from 1, if the medium is non-homogeneous or the object is positioned asymmetrically. The quotient can thus be compared with an upper and lower limit value. If the quotient is above the upper or below the lower limit value, the medium must be non-homogeneous or the object must be positioned asymmetrically. It can then be assumed with a high level of probability that the backscattering medium is not smoke. If in contrast the quotient is between the limit values, it must be smoke or an object that cannot be distinguished from smoke by this structure. Detection properties can be further improved, if the evaluation unit 4 records the pattern of the quotient over time and compares it with known patterns.

In a further embodiment (not illustrated) a number of transmitters 5, 5' and a number of receivers 9, 9' are present. The arrangement of the transmitters and receivers here can correspond to the arrangement described in WO 2009/103777. The sensor apparatus described there, with its differentiation, is particularly suitable for suppressing external light. As well as the advantage of suppressing external light particularly effectively, it is also possible, by comparing the received signals by quotient formation, to determine whether the light is backscattered by a fairly homogeneous smoke cloud or by an asymmetrically positioned object. In other words by forming the quotient or by forming a number of quotients, if more than just two inputs signals are available, additional information may be acquired.

Although radiation of the same wavelength is always used with the exemplary embodiments described above, in a further embodiment a number of transmitters are used, which emit light at a number of different wavelengths. FIG. 3 shows how the quantity of backscattered light is then a function wavelength and particle size. The intensity 16 of the scattered light is recorded here in any units over particle size 17 in nanometers.

The curve 18 shows this relationship for blue light with a wavelength of 450 nm. The curve 19 shows the relationship for infrared light in the region of 900 nm. A first auxiliary line 21 shows the point where the smoke particles are 300 nm in size. Smoke particles frequently have a size in this region, so this point is particularly significant.

It is easy to see that the quantity of light backscattered at the two wavelengths is very different. This phenomenon has a certain similarity to resonances, which occur when the size of the particle is in the region of the wavelength.

A second auxiliary line 22 corresponds to a very much bigger particle, for example a dust particle or another object. The phenomena observed with smaller objects do not occur here. If the object is large and white or light in color, the light with the two wavelengths is backscattered in an identical manner, as the reflection properties are not a function of wavelength. With smaller objects, for example smoke particles, the reflection properties are however a function of wavelength, even if the smoke appears white for example.

Of course it can come about that the scattering object is highly colored. The backscattered light at the two wavelengths is then different. It is then not possible to decide whether there is smoke or an object present.

It can also be verified whether the scattered light is received at a number of places with identical intensity. If the object is in a symmetrical position, it can also generate similar signals to those of smoke in this test. It cannot therefore be excluded that a highly colored object in a symmetrical position generates a false alarm. However since this event is relatively improbable, the probability of a false alarm can be greatly reduced.

Although the invention has been illustrated and described in detail using an exemplary embodiment, the invention is not limited to the disclosed examples and other variations can be derived therefrom by the person skilled in the art without departing from the scope of protection of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

What is claimed is:

1. A method for identifying an interference object in a scatter volume of an open optical fire detector which operates using at least two scattered light arrangements, comprising:
   converting measured radiation to scatter signals from a common scatter volume;
   evaluating the scatter signals, by comparison with one another, to identify a position of an interference object by determining a quotient of the scatter signals and comparing the quotient with lower and upper limit values,
   wherein each scattered light arrangement includes a transmitter and a receiver and in each scattered light arrangement at least one of a transmit characteristic of the transmitter and a receive characteristic of the receiver is essentially of the Lambert type and a main transmit direction of each transmitter and a main receive direction of each receiver are parallel.

2. The method as claimed in claim 1, wherein the scattered light arrangements differ from one another at least in arrangement of at least one optical component.

3. The method as claimed in claim 2, wherein a first transmitter and a receiver form a first scattered light arrangement and a second transmitter and the receiver form a second scattered light arrangement.

4. The method as claimed in claim 2, wherein a transmitter and a first receiver form a first scattered light arrangement and the transmitter and a second receiver form a second scattered light arrangement.

5. The method as claimed in claim 2, wherein a plurality of transmitters and a plurality of receivers are used.

6. The method as claimed in claim 5, wherein the transmitters emit radiation at different wavelengths.

7. The method as claimed in claim 6, wherein said evaluating of the scatter signals comprises:
   recording a pattern of the quotient over time; and
   comparing the pattern that has been recorded with known patterns.

8. The method as claimed in claim 1, wherein a first transmitter and a receiver form a first scattered light arrangement and a second transmitter and the receiver form a second scattered light arrangement.

9. The method as claimed in claim 1, wherein a transmitter and a first receiver form a first scattered light arrangement and the transmitter and a second receiver form a second scattered light arrangement.

10. The method as claimed in claim 1, wherein a plurality of transmitters and a plurality of receivers are used.

11. The method as claimed in claim 10, wherein transmitters emit radiation at different wavelengths.

12. The method as claimed in claim 11, wherein said evaluating of the scatter signals comprises:
    determining a quotient of the scatter signals; and
    comparing the quotient with lower and upper limit values.

13. The method as claimed in claim 12, wherein said evaluating of the scatter signals comprises:
    recording a pattern of the quotient over time; and
    comparing the pattern that has been recorded with known patterns.

14. An optical open fire detector, comprising:
    a detection unit, operating according to scattered light principles by converting measured radiation to scatter signals from a common scatter volume, having at least three optical components including at least one transmitter, having a transmit characteristic essentially of the Lambert type, and at least one receiver having a receive characteristic essentially of the Lambert type and a main transmit direction of each transmitter and a main receive direction of each receiver in parallel; and
    an electronic evaluation unit including a programmed processor, connected to the detection unit, evaluating the scatter signals, by comparison with one another, to identify a position of an interference object by determining a quotient of the scatter signals and comparing the quotient with lower and upper limit values.

15. The optical open fire detector as claimed in claim 14, wherein a first transmitter and a receiver form a first scattered light arrangement and a second transmitter and the receiver form a second scattered light arrangement.

16. The optical open fire detector as claimed in claim 14, wherein a transmitter and a first receiver form a first scattered light arrangement and the transmitter and a second receiver form a second scattered light arrangement.

17. The optical open fire detector as claimed in claim 14, wherein detection unit includes a plurality of transmitters and a plurality of receivers.

18. The optical open fire detector as claimed in claim 17, wherein the transmitters emit radiation at different wavelengths.

19. The optical open fire detector as claimed in claim 18, wherein said electronic evaluation unit further includes a storage storing a pattern of the quotient over time and the processor compares the pattern stored in the storage with known patterns.

* * * * *